(12) United States Patent
McGuinness et al.

(10) Patent No.: US 10,179,754 B2
(45) Date of Patent: Jan. 15, 2019

(54) PROCESS FOR THE ISOMERISATION OF C3-7 (HYDRO)(HALO)FLUOROALKENES

(71) Applicant: MEXICHEM AMANCO HOLDING S.A. DE C.V., Tlalnapantla (MX)

(72) Inventors: Claire E McGuinness, Cheshire (GB); Andrew P Sharratt, Cheshire (GB)

(73) Assignee: MEXICHEM AMANCO HOLDING S.A. de C.V., Tlalnepantla (MX)

( * ) Notice: Subject to any disclaimer, the term of this patent is extended or adjusted under 35 U.S.C. 154(b) by 0 days.

(21) Appl. No.: 15/030,940

(22) PCT Filed: Oct. 24, 2014

(86) PCT No.: PCT/GB2014/053188
§ 371 (c)(1),
(2) Date: Apr. 21, 2016

(87) PCT Pub. No.: WO2015/059500
PCT Pub. Date: Apr. 30, 2015

(65) Prior Publication Data
US 2016/0332939 A1 Nov. 17, 2016

(30) Foreign Application Priority Data
Oct. 25, 2013 (GB) .................................. 1318888.3

(51) Int. Cl.
| | | |
|---|---|---|
| *C07C 17/358* | (2006.01) | |
| *C07C 17/25* | (2006.01) | |
| *C07C 21/18* | (2006.01) | |
| *B01J 21/04* | (2006.01) | |
| *B01J 23/26* | (2006.01) | |
| *B01J 21/06* | (2006.01) | |
| *C01F 7/02* | (2006.01) | |

(52) U.S. Cl.
CPC ............ *C07C 17/358* (2013.01); *B01J 21/04* (2013.01); *B01J 21/066* (2013.01); *B01J 23/26* (2013.01); *C01F 7/02* (2013.01); *C07C 17/25* (2013.01); *C07B 2200/09* (2013.01)

(58) Field of Classification Search
CPC .................................................. C07C 17/358
See application file for complete search history.

(56) References Cited

U.S. PATENT DOCUMENTS

| | | | |
|---|---|---|---|
| 1,868,869 A | 7/1930 | Barnitt | |
| 2,015,593 A | 9/1935 | Derr | |
| 2,499,675 A | 12/1945 | Owen | |
| 3,201,199 A * | 8/1965 | Lindsay | C01F 7/144 423/127 |
| 3,223,483 A * | 12/1965 | Osment | B01J 20/08 423/131 |
| 8,513,473 B2 * | 8/2013 | Sakyu | C07C 17/358 570/151 |
| 2007/0037704 A1 | 2/2007 | Rizkalla | |
| 2009/0299107 A1 | 12/2009 | Wang et al. | |
| 2010/0022809 A1 * | 1/2010 | Cottrell | C07C 17/25 570/163 |
| 2010/0163781 A1 * | 7/2010 | Sharratt | C07C 17/358 252/67 |
| 2010/0197980 A1 * | 8/2010 | Nappa | C07C 17/358 570/151 |
| 2010/0256426 A1 | 10/2010 | Sakyo et al. | |
| 2011/0112338 A1 | 5/2011 | Smith et al. | |
| 2011/0282112 A1 | 11/2011 | Nappa et al. | |
| 2012/0059200 A1 | 3/2012 | Pokrovski et al. | |
| 2012/0172639 A1 | 7/2012 | Nappa et al. | |
| 2014/0336424 A1 * | 11/2014 | Okamoto | C07C 17/358 570/151 |

FOREIGN PATENT DOCUMENTS

| | | |
|---|---|---|
| EP | 1900716 | 3/2008 |
| EP | 1918269 | 5/2008 |
| EP | 2778150 | 9/2014 |
| FR | 2989374 | 10/2013 |
| JP | 2009091301 | 4/2009 |
| WO | WO2008/008350 | 1/2008 |
| WO | WO2008/030443 | 3/2008 |
| WO | WO2008/125825 | 10/2008 |
| WO | WO2009/026082 | 2/2009 |
| WO | WO2010/141664 | 12/2010 |
| WO | WO2013/077189 | 5/2013 |
| WO | WO2014/003068 | 1/2014 |

OTHER PUBLICATIONS

JP2009091301, Apr. 2009, pp. 1-6; English translation.*
FR2989374, Oct. 2013, pp. 1-4; English translation.*
Sumitomo Chemical, Product Databook, Dec. 2015, pp. 1-16.*
Written Opinion of the International Searching Authority dated Apr. 30, 2015 in PCT/GB2014/053188; 7 pages.
International Search Report dated Feb. 26, 2015 in PCT/GB2014/053188; 4 pages.
Prosecution History of Priority Application GB1318888.3 (146 pages).
Kirk-Othmer Encyclopedia of Chemical Technology, Fifth Edition, vol. 2, 2004 pp. 391-398.
Matar et al.. Catalysis in Petrochemical Processes, Kluwer Academic Publishers, 1989; p. 118.
Poisson et al., Alumina, Catalyst Supports and Supported Catalysts, Theoretical and Applied Concepts, Alvin B. Stiles, pp. 11-55; 1987.
Goodboy et al., Production Processes, Properties, and Applications for Activated and Catalytic Aluminas, Alumina Chemicals (Science and Technology Handbook), pp. 93-98, 1990.
Briggs, Pelleted Catalyst Systems. Alumina Chemicals, Science and Technology Handbook; p. 289; 1990.
Matar et al., Catalysis in Petrochemical Processes;Kluwer Academic Publishers, Netherlands, 1989; p. 118.

* cited by examiner

*Primary Examiner* — Medhanit W Bahta
(74) *Attorney, Agent, or Firm* — Ryan Kromholz & Manion, S.C.

(57) ABSTRACT

The present invention relates to a process for isomerizing a $C_{3-7}$ (hydro)(halo)fluoroalkene comprising (a) providing a reactor feed stream comprising the $C_{3-7}$ (hydro)(halo)fluoroalkene; and (b) contacting the $C_{3-7}$ (hydro)(halo)fluoroalkene with a catalyst comprising alumina to isomerize the $C_{3-7}$ (hydro)(halo)fluoroalkene, wherein the catalyst has a sodium content of less than about 800 ppm.

34 Claims, No Drawings

PROCESS FOR THE ISOMERISATION OF C3-7 (HYDRO)(HALO)FLUOROALKENES

The present invention relates to a process for isomerising (hydro)(halo)fluoroalkenes and particularly to catalytic $C_{3-7}$ (hydro)(halo)fluoroalkene isomerisation.

The listing or discussion of information or a prior-published document in this specification should not necessarily be taken as an acknowledgement that the information or document is part of the state of the art or is common general knowledge.

Many (hydro)(halo)fluoroalkenes can exist as structural isomers or geometric isomers. Geometric isomerism, which is also known as cis/trans or E/Z isomerism, depends on the arrangement of the substituents around the double bond. For example 1,3,3,3-tetrafluoropropene (1234ze) and 2,3,3,3-tetrafluoropropene (1234yf) are structural isomers of each other. 1234ze also exists as two geometric isomers cis-1,3,3,3-tetrafluoropropene (1234ze(Z)) and trans-1,3,3,3-tetrafluoropropene (1234ze(E)).

Geometric isomers typically have differing physical (e.g. boiling point) and/or chemical properties (e.g. reactivity). These differing properties may be attributed to the fact that the dipole moment of the substituents will tend to add for a cis isomer, while for a trans isomer, the dipoles of the substituents will tend to cancel each other out. As a result of the differing physical and/or chemical properties of cis/trans isomers, one of the isomers may be preferred over the other for a particular application. Thus, it may be desirable to be able to convert one cis/trans isomer to the other.

In processes for preparing alkenes such as (hydro)(halo) fluoroalkenes that exist as geometric isomers, both of the cis/trans isomers will typically be formed. The amount of each cis/trans isomer formed may depend on a number of factors, such as the kinetic and thermodynamic stability of each cis/trans isomer. If one isomer is preferred over the other then depending on the utility of the (hydro)(halo) fluoroalkenes, it may then be desirable to convert one cis/trans isomer to the other. Alternatively, it may be desirable during the process for preparing alkenes such as (hydro) (halo)fluoroalkenes to isomerise one cis/trans isomer to the other (preferred) cis/trans isomer.

WO 2008/008351 describes that it is possible to increase the ratio of the Z to E isomers in 1,2,3,3,3-pentafluoropropene. This is said to be possible using a catalyst supported on $AlF_3$ or carbon, which catalyst is selected from $SbCl_wF_{5-w}$, $TiCl_xF_{4-x}$, $SnCl_yF_{4-y}$, and $TaCl_zF_{5-z}$, wherein w is from 0 to 4, x is from 0 to 3, y is from 0 to 3 and z is from 0 to 4. Further, in the Examples of WO 2008/030443 there is described the partial isomerisation of 1234ze(E) to 1234ze (Z) over a crushed chromium oxide gel pellet catalyst.

WO 2008/125825 is directed to a process for isomerising a (hydrohalo)fluoroalkene. The process comprising contacting the (hydrohalo)fluoroalkene with a catalyst comprising an unsupported Lewis acid, a chromia-containing catalyst containing at least one additional metal, an alumina, a supported liquid catalyst, and mixtures thereof.

EP-A-1,918,269 concerns a process for converting 1234ze(Z) to 1234ze(E) using a metal-based catalyst selected from the group consisting of halogenated metal oxides, Lewis acid metal halides, zero-valent metals, and combinations thereof.

Notwithstanding the above processes, catalytic dehydrohalogenation has its problems, one of which is because the chemistry is thought inherently to foul the catalyst. Catalyst fouling typically is controlled by one or more of (a) using the mildest conditions possible, and (b) limiting the exposure of the catalyst to high partial pressure of unsaturates.

The use of measure (b) above is inherently very limited in the catalytic isomerisation of (hydro)(halo)fluoroalkenes. Consequently, operating cycles and catalyst life are believed generally to be relatively short compared to, for example, (hydro)fluorination chemistry. Short operating cycles and catalyst life require more frequent catalyst regeneration, or simply more catalyst, each of which have cost implications.

Thus, there is a need for an economic process for preparing $C_{3-7}$ (hydro)(halo)fluoroalkenes using highly active and stable catalysts.

The invention addresses the foregoing and other deficiencies by the provision of a process for isomerising a $C_{3-7}$ (hydro)(halo)fluoroalkene comprising (a) providing a reactor feed comprising the $C_{3-7}$ (hydro)(halo)fluoroalkene; and (b) contacting the $C_{3-7}$ (hydro)(halo)fluoroalkene with a catalyst comprising alumina to isomerise the $C_{3-7}$ (hydro) (halo)fluoroalkene, wherein the catalyst has a sodium content of less than about 800 ppm.

Preferably, the sodium content of the catalyst is less than 500 ppm, more preferably less than 400 ppm, 300 ppm, 200 ppm or 150 ppm. It is especially preferred that the catalyst has a sodium content of less than 100, 80, 60 or 40 ppm. The catalyst used in the process of the invention may contain less than 30, 20 or 10 ppm.

The low sodium alumina-based catalyst of the invention may contain additional components. In a preferred embodiment, the low sodium alumina-based catalyst comprises a metal oxide supported on the alumina.

The sodium content of the catalysts of the invention can be measured by any suitable known method. Particularly useful methods include atomic absorption (AAS) and optical emission spectroscopy (OES), such as inductively coupled plasma optical emission spectroscopy (ICP-OES). The sodium analysis used in the examples herein was performed by London and Scandanavian Metallurgical Company of Yorkshire, England using ICP-OES.

We refer above to the sodium content of the catalyst of the invention. When the catalyst comprises a metal oxide supported on alumina, the amount sodium referred to above can correspond also to sodium content of the alumina support. This is because, as discussed in more detail below, any sodium that is present in the catalyst typically arises from the preparation of the alumina which forms the support of the catalyst. In other words, the metal oxide may contain little or no (measurable) sodium.

In an embodiment, however, there may be measurable sodium content in the metal oxide of the catalyst (as opposed to, or more likely in addition to, any sodium content in the alumina support). For example, chromia typically includes measurable amounts of sodium, for example when the chromia has been made from sodium salts.

Without being bound by theory, it is believed that the low sodium content of the catalysts of the subject invention increases the availability of Lewis acid sites in the catalyst, for example in the alumina (support), that are required for the isomerisation reaction on the invention.

In another embodiment, the catalysts used in the subject invention contain low amounts of other alkali metals and/or low amounts of alkaline earth metals. By "low amounts" we include the amounts referred to above in connection with sodium.

When the catalyst comprises a metal oxide supported on alumina, the catalyst typically contains at least about 50% by weight of the alumina support, based on the total weight of the catalyst. In one aspect, the catalyst contains at least about 60% by weight of the alumina support, preferably at least about 70% by weight, for example at least about 80% by weight.

When present, the metal oxide typically makes up less than about 50% by weight of the catalyst, based on the total weight of the catalyst. In one embodiment, the catalyst contains up to about 40% by weight of the metal oxide, preferably up to about 30% by weight, for example up to about 20% by weight.

Typically, the metal in the metal oxide is any metal that forms a metal (oxy)fluoride which has Lewis acid character. Examples are metals selected from Sc, Y, Ti, Zr, Hf, V, Nb, Ta, Cr, Mo, W, Mn, Re, Fe, Ru, Co, Rh, Ir, Ni, Pd, Pt, Cu, Ag, Au, Zn, La and Ce. Preferably, the metal is a transition metal, such as Cr, Zr, Nb, Ta, V, Mo, Ni or Co. In a preferred embodiment, the metal is zirconium or chromium.

The catalyst used in the process of the invention may contain at least one additional metal or compound thereof in addition to the metal oxide. This can also be referred to as a metal promoter. In one embodiment, the at least one additional metal is selected from Sc, Y, Ti, Zr, Hf, V, Nb, Ta, Cr, Mo, W, Mn, Re, Fe, Ru, Co, Rh, Ir, Ni, Pd, Pt, Cu, Ag, Au, Zn, La and Ce. Preferably, the at least one additional metal is selected from Zn, Zr, Cr, In, Co and Ni.

For the avoidance of doubt, the additional metal (or compound thereof) cannot be the same as the metal of the metal oxide for any given catalyst. For example, if the catalyst comprises an oxide of chromium supported on alumina, the at least one additional metal can be any suitable metal, including the metals listed in the preceding paragraph, other than chromium.

In a preferred aspect, the compound of the additional metal is an oxide, fluoride or oxyfluoride, of the additional metal.

When present, the total amount of the additional metal or the compound of the additional metal present in the catalysts of the invention is typically from about 0.01% to about 25% by weight, based on the total weight of the catalyst. Preferred amounts of the additional metal or the compound of additional metal are from about 0.1% to about 20%, conveniently from about 0.1% to about 15%. In some embodiments, the catalysts contain the additional metal or the compound of additional metal in an amount of from about 0.5% by weight to about 10% by weight of the catalyst, such as from about 1 to about 8% by weight of the catalyst, e.g. about 1 to about 5% by weight.

It is to be understood that the amount of additional metal or the compound of the additional metal quoted herein refers to the amount of elemental metal, whether present as elemental metal or as a compound of the metal.

Any suitable alumina may be used for the catalyst providing that it results in a catalyst that has the low amounts of sodium specified herein. Such alumina is available commercially from, for example, BASF or ASM Catalysts LLC. The alumina may be prepared by, for example, precipitation from a solution of ammonia with a suitable aluminium salt, such as aluminium nitrate.

The catalysts comprising a metal oxide supported on alumina may be made by impregnating commercially available low sodium alumina with the metal oxide, and optionally any additional metal or compound thereof. This may be achieved by any suitable means known in the art of catalyst manufacture, for example by impregnating the alumina with a suitable precursor metal salt or salts from which the metal oxide (and any additional metal or compound thereof) can be readily generated with thermochemical processing.

By way of example, chromia cannot be directly impregnated into alumina. Typically, therefore, a chromium salt is used for impregnation that is soluble in water or another suitable solvent. Suitable chromium salts include chromium (III) nitrate and hexaaquachromium complexes such as $Cr(H_2O)_6.Cl_3$. Following impregnation of the chromium salt in a suitable solvent, and before use, the catalyst is calcined in air and/or nitrogen at temperatures of, for example, 150 to 500° C. An example of the preparation of such a catalyst is described in EP-A-366797, which is incorporated herein by reference.

Alternatively, the catalysts comprising a metal oxide supported on alumina may be prepared by co-precipitation of a suitable aluminium precursor salt or salts with a suitable precursor metal salt of the metal oxide (and any additional metal or compound thereof) in a solvent such as water on the addition of ammonia or ammonium hydroxide. Thermochemical processing (e.g. calcining) of the resulting precipitated product yields the desired catalyst.

Another method of preparing the catalysts comprising a metal oxide supported on alumina is by vapour deposition. This involves impregnating the support by contacting it with the vapours of suitably volatile metal compounds. It may be desirable to heat the support during this contacting to effect decomposition of the vapour, thereby allowing the active metal compound to impregnate the support. Suitably volatile compounds include alkyl compounds such as dimethyl zinc or carbonyl complexes such as chromium hexacarbonyl. See for example, "The design and Preparation of Supported Catalysts", G. J. K. Acres et al, Catalysis, 1981 (RSC), which is incorporated herein by reference.

Examples of catalysts used in the subject invention include alumina and chromia or zirconia supported on alumina, i.e. chromium oxide or zirconium oxide supported on alumina. Prior to contacting with the $C_{3-7}$ (hydro)(halo)fluoroalkane to effect isomerisation, the catalyst used in the subject invention typically is pre-treated by fluorination. Such pre-treatment is known in the art and generally involves drying the catalyst under nitrogen gas at elevated temperature followed by pre-fluorination with HF (optionally diluted with nitrogen) at elevated temperature.

Consequently, although the original catalyst (also referred to as the pre-catalyst) is alumina or a metal oxide (e.g. chromia or zirconia) supported on (low sodium) alumina, the catalyst used at the start of dehydrohalogenation typically is partially or fully fluorinated alumina or partially or fully fluorinated metal oxide (i.e. a metal oxyfluoride or a metal fluoride) supported on a partially or fully fluorinated alumina (e.g. an alumina oxyfluoride or alumina fluoride). This is because during pre-treatment at least some of the oxygen atoms in the catalyst are replaced by fluorine atoms.

The catalysts used in the present invention may be amorphous. By this we mean that the catalyst does not demonstrate substantial crystalline characteristics when analysed by, for example, X-ray diffraction. Alternatively, the catalysts may exhibit some crystalline character, in the alumina (support) and/or the metal oxide.

The catalysts of the invention typically have a surface area of at least 50 $m^2/g$, for example from 50 to about 350 or 400 $m^2/g$, preferably from about 70 to about 250 $m^2/g$, such as from about 100 to about 200 $m^2/g$, before they are subjected to pre-treatment. The pre-fluorination treatment typically has the effect of lowering the surface area of the catalyst. After the pre-fluorination treatment the catalysts of the invention typically have a surface area of from about 10 to about 300 $m^2/g$, preferably from about 20 to about 200 $m^2/g$, such as from about 50 to 150 $m^2/g$.

The catalysts of the invention may be provided in any suitable form known in the art. For example, they may be provided in the form of pellets or granules of appropriate size for use in a fixed bed or a fluidised bed.

The catalysts of the invention may contain additives such as binders and/or lubricants to improve the physical integrity of the catalyst during its granulation or shaping into the desired form. When used, binders and/or lubricants typically make up about 0.05 to 10% by weight of the catalyst, for example from about 0.1 to about 5% by weight. An example of a suitable binder and/or lubricant is graphite.

In use, the catalyst may be regenerated or reactivated periodically by heating in air at a temperature of from about 300° C. to about 500° C. Air may be used as a mixture with an inert gas such as nitrogen or with hydrogen fluoride, which emerges hot from the catalyst treatment process and may be used directly in fluorination processes employing the reactivated catalyst. It has been found that the spent catalyst from the process of the invention typically is unexpectedly easy to regenerate compared to known alumina catalysts. The chromia supported on alumina low sodium catalyst of the invention is believed to be particularly easy to regenerate.

Typically, the process of the invention comprises contacting the $C_{3-7}$ (hydro)(halo)fluoroalkene with the low sodium alumina-based catalyst in the vapour or liquid phase (preferably the vapour phase) and may be carried out at a temperature of from about 0 to about 400° C., e.g. from about 50 to about 400° C. The process may be carried out at atmospheric, sub- or super atmospheric pressure, preferably up to about 30 bara, for example from about 1 to about 25 bara.

Preferably, the (hydro)(halo)fluoroalkene is contacted with the low sodium alumina-supported metal oxide catalyst in the vapour phase at a temperature of from about 50 to about 360° C., more preferably from about 80 to about 320° C., such as from about 100 to about 300° C. In some embodiments, the preferred reaction temperature is from about 120° C. to about 360° C., for example from about 130° C. to about 340° C. Preferably, the process is conducted at a pressure of from about 1 to about 20 bara. Of course, the skilled person will appreciate that the preferred conditions (e.g. temperature, pressure for conducting the process of the invention may vary (even outside the above ranges) depending on the nature of the (hydro)(halo)fluoroalkene and the catalyst being employed.

The contact time for the $C_{3-7}$ (hydro)(halo)fluoroalkene with the low sodium alumina-supported metal oxide catalyst can vary widely depending on reactor and catalyst volume and reaction temperatures and pressures. Typically, the contact time ranges from about 0.1 second to about 1000 seconds, for example from about 1 second to about 800 seconds. Preferably, the contact time is from about 2 to about 500 seconds.

The process of the invention can be carried out in any suitable apparatus, such as a static mixer, a stirred tank reactor or a stirred vapour-liquid disengagement vessel. The process may be carried out batch-wise, or continuously. Either the batch-wise process or the continuous process may be carried out in a "one-pot" fashion, or using two or more discrete reaction zones and/or reaction vessels. Preferably, the process of the invention is a continuous process. Of course, even in a "continuous" process, the skilled person will appreciate that the process will need to be paused periodically, e.g. for maintenance and/or catalyst regeneration.

Preferably, the isomerisation is be carried out in the absence of an HF feed. However, it may be desirable in certain embodiments to use some HF in order to prevent and/or retard excessive decomposition of the organic feed and/or coking of the catalyst. Typically, the molar HF:organics ratio in the process of the invention if an HF feed is utilised will range from about 0.01:1 to about 1:1, preferably from about 0.1:1 to about 1:1, more preferably from about 0.5:1 to about 1:1.

Unless otherwise stated, as used herein, a (hydro)(halo)fluoroalkene is an alkene in which at least one of the hydrogen substituents has been replaced by a fluorine substituent and, optionally, at least one halogen substituent selected from chlorine, bromine and iodine. In other words, the definition of a (hydro)(halo)fluoroalkene includes:

a hydrofluoroalkene (i.e. an alkene in which at least one but not all of the hydrogen substituents has been replaced by a fluorine substituent);

a halofluoroalkene (i.e. an alkene in which all of the hydrogen substituents have been replaced by a fluorine substituent or by a halogen substituent selected from chlorine, bromine and iodine, provided that not all of the substituents are the same); and a hydrohalofluoroalkene (i.e. an alkene in which at least one but not all of the hydrogen substituents has been replaced by a fluorine substituent and by a halogen substituent selected from chlorine, bromine and iodine).

Correspondingly, as used herein, the term hydro(halo)fluoroalkene is an alkene in which at least one but not all of the hydrogen substituents has been replaced by a fluorine substituent and, optionally, at least one halogen substituent selected from chlorine, bromine and iodine. In other words, the definition of a hydro(halo)fluoroalkene includes a hydrofluoroalkene and a hydrohaloalkene as defined above.

For the avoidance of doubt, as used herein, any reference to a $C_{3-7}$ (hydro)(halo)fluoroalkene, $C_{3-7}$ hydro(halo)fluoroalkene, a $C_{3-7}$ hydrofluoroalkene, a $C_{3-7}$ halofluoroalkene or a $C_{3-7}$ hydrohalofluoroalkene refers to a (hydro)(halo)fluoroalkene, hydro(halo)fluoroalkene, hydrofluoroalkene, halofluoroalkene or hydrohalofluoroalkene having from 3 to 7 carbon atoms, e.g. a hydro(halo)fluoro propene, butene, pentene, hexene or heptene.

The conversion of $C_{3-7}$ (hydro)(halo)fluoroalkene in its isomerisation according to the process of the invention typically is at least about 5%, preferably at least about 50%, more preferably at least about 75%, for example at least about 85% or about 95% (based on the total molar amount of $C_{3-7}$ (hydro)(halo)fluoroalkene in the reactor feed stream).

The $C_{3-7}$ (hydro)(halo)fluoroalkenes isomerised by the process of the invention contain a carbon-carbon double bond and may thus exist as E (entgegen) and Z (zusammen) geometric isomers about each individual double bond.

Preferably, the $C_{3-7}$ (hydro)(halo)fluoroalkene isomerised by the process of the invention exists as geometric isomers and the process of the invention results in a change in a ratio of the E and Z isomers. In one aspect of the invention, the selectivity of conversion from one (geometric) isomer to the other during the isomerisation process of the invention is at least about 70%, preferably at least about 80%, more preferably at least about 90%.

In a preferred embodiment, the $C_{3-7}$ (hydro)(halo)fluoroalkene isomerised by the process of the invention is a $C_{3-7}$ hydro(halo)fluoroalkene, i.e. a $C_{3-7}$ hydrofluoroalkene or a $C_{3-7}$ hydrohalofluoroalkene.

In one embodiment, the $C_{3-7}$ (hydro)(halo)fluoroalkene isomerised by the process of the invention is a $C_{3-6}$ (hydro)(halo)fluoroalkene. The process of the invention is particularly suited to isomerising $C_{3-4}$ (hydro)(halo)fluoroalkenes.

In one aspect of the invention, the $C_{3-7}$ (hydro)(halo) fluoroalkene isomerised by the process of the invention is a (hydro)(halo)fluoropropene, i.e. a hydrofluoropropene, a halofluoropropene or a hydrohalofluoropropene. Preferably, the (hydro)(halo)fluoropropene is a hydrofluoropropene or a hydrohalofluoropropene.

Advantageously, the hydrofluoropropene is selected from trifluoropropenes, tetrafluoropropenes and pentafluoropropenes.

1,3,3-trifluoropropene ($CF_2HCH=CHF$) is an example of a trifluoropropene that can be isomerised according to the process of the invention.

In a preferred embodiment, the hydrofluoropropene is selected from tetrafluoropropenes and pentafluoropropenes.

1,3,3,3-tetrafluoropropene (1234ze) is an example of a tetrafluoropropene that can be isomerised according to the process of the invention. The low sodium catalysts described herein are particularly effective at isomerising cis-1,3,3,3-tetrafluoropropene (1234ze(Z)) to trans-1,3,3,3-tetrafluoropropene (1234ze(E)).

1,2,3,3,3-pentafluoropropene (1225ye) is an example of a pentafluoropropene that can be isomerised according to the process of the invention. The low sodium catalysts described herein are also surprisingly effective at isomerising E-1,2,3,3,3-pentafluoropropene (1225ye(E)) to Z-1,2,3,3,3-pentafluoropropene (1225ye(Z)).

1-chloro-3,3,3-trifluoropropene (1233zd) is an example of a hydrohalofluoropropene that can be isomerised according to the process of the invention. The process of the invention is effective for isomerising cis-1-chloro-3,3,3-trifluoropropene (1233zd(Z)) to trans-1-chloro-3,3,3-trifluoropropene (1233zd(E)).

In one aspect of the invention, the $C_{3-7}$ (hydro)(halo) fluoroalkene isomerised by the process of the invention is a (hydro)(halo)fluorobutene, i.e. a hydrofluorobutene, a halofluorobutene or a hydrohalofluorobutene. Preferably, the (hydro)(halo)fluorobutene is a hydrofluorobutene or a hydrohalofluorobutene.

1,1,1,4,4,4-hexafluorobut-2-ene (1336mzz) is an example of a hydrofluorobutene that can be isomerised according to the process of the invention. The process of the invention is effective for isomerising cis-1,1,1,4,4,4-hexafluorobut-2-ene (1336mzz(Z)) to trans-1,1,1,4,4,4-hexafluorobut-2-ene (1336mzz(E)).

A wide variety of process streams may be used as the reactor feed stream for the process of the invention. Various other molecules or materials can make up the balance of the feed stream in the process of the present invention without having a deleterious effect on the claimed isomerisation. For example, it is contemplated that the feed stream in the process of the invention may originate as the effluent from an upstream process, as may exist, for example, in a commercial plant for producing fluorinated olefins. In one embodiment, the feed stream is the effluent, or at least a part of the effluent, from one or more upstream reactions which produce product stream(s) comprising an un-reacted halogenated alkane (e.g. un-reacted fluorinated and/or chlorinated propanes) and a $C_{3-7}$ (hydro)(halo)fluoroalkene, such as a (hydro)(halo)propene.

By way of more specific but non-limiting example, 1234ze may be prepared by the dehydrofluorination of 1,1,1,3,3-pentafluoropropane (245fa). The dehydrofluorination reaction product stream typically contains a proportion of un-reacted 245fa and a combination of cis-1,3,3,3 tetrafluoropropene (1234ze(Z)) and trans-1,3,3,3-tetrafluoropropene (1234ze(E)), together with HF. One embodiment of the invention includes converting the cis-form of fluorinated olefin in such a stream (1234ze(Z) in this example) and/or other similar streams which have been processed (by separation of HF and/or 1234ze(E), for instance) from this or similar reaction product streams to the trans-form (1234ze(E) in this example).

Accordingly, the invention provides a process for preparing a $C_{3-7}$ (hydro)(halo)fluoroalkene by dehydrohalogenation of a reactor feed comprising $C_{3-7}$ hydro(halo)fluoroalkane, the process further comprising a process for isomerising a $C_{3-7}$ (hydro)(halo)fluoroalkene as described herein.

When the dehydrohalogenation reactor feed comprises 1,1,1,3,3-pentafluoropropane (245fa), the process for preparing the $C_{3-7}$ (hydro)(halo)fluoroalkene comprises the following steps:

(a) dehydrofluorinating 245fa to produce a dehydrohalogenation stream comprising 1234ze(Z), 1234ze(E), HF and, optionally, unreacted 245fa;

(b) optionally recovering the HF from the dehydrohalogenation stream;

(c) optionally recovering 1234ze(E) from the dehydrohalogenation stream; and (d) contacting the dehydrohalogenation stream with the catalyst comprising alumina to isomerise the 1234ze(Z) to 1234ze(E), wherein the catalyst has a sodium content of less than about 800 ppm.

Suitable catalysts, reaction conditions, separation techniques, etc. for the dehydrofluorination of 245fa step (a), and optional recovery steps (b) and (c), are described in, for example, U.S. Pat. No. 6,124,510, JP11-140002, EP-A-1900716 and International application no. PCT/GB2013/051129, each of which are incorporated herein by reference. For the avoidance of doubt, it is to be understood that suitable and preferred catalysts, reaction conditions etc. for step (d) are those described herein in connection with the isomerisation process of the invention.

It will be evident from the foregoing that the amount of $C_{3-7}$ (hydro)(halo)fluoroalkene in the reactor feed stream of the isomerisation process of the invention can vary widely, typically from about 1% by weight to 100% by weight of the feed stream, depending on the nature of the feed stream. Preferably, the reactor feed stream contains at least about 5% by weight of the $C_{3-7}$ (hydro)(halo)fluoroalkene, such as at least about 10% or at least about 15% by weight. In some embodiments, the reactor feed stream contains at least about 20%, 30%, 40% or 50% by weight of the $C_{3-7}$ (hydro)(halo) fluoroalkene.

The invention further provides the use of a catalyst comprising alumina, wherein the catalyst has a sodium content of less than about 800 ppm, in the isomerisation of a $C_{3-7}$ (hydro)(halo)fluoroalkene. Typically, the use comprises the provision of a reactor feed stream comprising the $C_{3-7}$ (hydro)(halo)fluoroalkene and contacting the $C_{3-7}$ (hydro)(halo)fluoroalkene from said feed with the catalyst. For the avoidance of doubt, any of the disclosure herein relating the isomerisation process of the invention applies equally to the above-described use of the invention.

The invention is further described with reference to the following non-limiting examples.

EXAMPLE 1

Isomerisation of 1234ze(Z) to 1234ze(E) with Alumina-Supported Chromia Catalysts High and low sodium alumina-supported chromia catalysts were compared in the isomerisation of cis-1,3,3,3- tetrafluoropropene (1234ze(Z)) to trans-1,3,3,3-tetrafluoropropene (1234ze(E)). The catalysts were a low sodium (350 ppm) alumina coated with nominally 10% $Cr_2O_3$ (referred to as catalyst 1), and a high sodium (2170 ppm) alumina coated with nominally 10% $Cr_2O_3$ (referred to as catalyst 2).

Both catalysts were dried at 250° C. with 60 mls/min nitrogen for an hour, followed by one hour at 360° C. with 60 mls/min nitrogen to calcine the catalyst. The catalysts were then pre-fluorinated, firstly by passing over the catalysts a mixture of HF at 30 mls/min diluted with 60 mls/min nitrogen at 300° C. for one hour. The nitrogen flow was then switched off, and HF was passed over the catalysts at 30 mls/min for one hour at 360° C. The HF was then switched off and the nitrogen purge switched back on to remove any traces of HF.

20 mls/min of 1234ze(Z) was then passed over each catalyst at 100° C. and samples of the reactor off gas were analysed by gas chromatography. The experiments were duplicated and the results are shown below.

| Catalyst number | Reactor off gas 1234ze(Z) | (mol %) 1234ze(E) |
|---|---|---|
| 1 (low Na) | 9.76 | 89.01 |
|  | 9.95 | 89.34 |
| 2 (high Na) | 66.34 | 32.69 |
|  | 67.76 | 32.24 |

It is evident from the above that the low sodium catalyst is considerably more active than the corresponding high sodium catalyst for the isomerisation of 1234ze(Z) to 1234ze(E).

EXAMPLE 2

Isomerisation of 1336Mzz(Z) to 1336Mzz(E) with Alumina-Supported Chromia Catalysts The same high and low sodium alumina-supported chromia catalysts used in Example 1 were compared in the isomerisation of cis-1,1,1,4,4,4-hexafluorobut-2-ene (1336mzz(Z)) to trans-1,1,1,4,4,4-hexafluorobut-2-ene (1336mzz(E)).

Both catalysts were dried at 200° C. with 60 mls/min nitrogen for 16 hours, followed by one hour at 360° C. and 60 mls/min $N_2$ to calcine the catalyst The catalysts were then pre-fluorinated, firstly by passing over the catalysts a mixture of HF at 60 mls/min diluted with 60 mls/min nitrogen at 300° C. for one hour. The nitrogen flow was then switched off, and HF was passed over the catalysts at 60 mls/min for one hour at 360° C. The HF was then switched off and the nitrogen purge switched back on to remove any traces of HF.

30 g of 1336mzz(Z) was added to a tube with a dip pipe. Nitrogen was passed through the dip pipe and bubbled through the 1336mzz(Z). Timed samples were taken of the resulting nitrogen/organic flow and the flow rate could be calculated. 3 mls/min 1336mzz(Z) and 15 mls/min nitrogen were passed to the reactors at varying reactor temperatures. Samples of the reactor off gas were analysed by GC and the following results were obtained.

Catalyst 1 (Low Na)

| | T (° C.) | | | | | | | |
|---|---|---|---|---|---|---|---|---|
| | 150 | 160 | 170 | 180 | 220 | 250 | 270 | 280 |
| 1336mzz(E) (mol %) | 5.25 | 7.22 | 9.92 | 59.82 | 76.80 | 85.01 | 88.67 | 90.20 |
| 1336mzz(Z) (mol %) | 87.10 | 83.07 | 81.09 | 33.18 | 16.80 | 10.42 | 6.11 | 4.25 |

Catalyst 2 (High Na)

| | T (° C.) | | | | |
|---|---|---|---|---|---|
| | 180 | 250 | 275 | 300 | 325 |
| 1336mzz(E) (mol %) | 0.00 | 1.34 | 1.88 | 11.68 | 55.57 |
| 1336mzz(Z) (mol %) | 100.0 | 98.66 | 97.81 | 88.32 | 44.43 |

It is evident from the above that the low sodium catalyst is considerably more active than the corresponding high sodium catalyst for the isomerisation of 1336mzz (Z) to 1336mzz (E).

EXAMPLE 3

Isomerisation of 1233zd (Z) to 1233zd(E) with Alumina-Supported

Chromia Catalysts

The same high and low sodium alumina-supported chromia catalysts used in Example 1 were compared in the isomerisation of cis-1-chloro-3,3,3-trifluoropropene (1233zd (Z)) to trans-1-chloro-3,3,3-trifluoropropene (1233zd(E)).

Both catalysts were dried at 200° C. with 60 mls/min nitrogen for 16 hours, followed by one hour at 360° C. and 60 mls/min $N_2$ to calcine the catalyst The catalysts were then pre-fluorinated, firstly by passing over the catalysts a mixture of HF at 60 mls/min diluted with 60 mls/min nitrogen at 300° C. for one hour. The nitrogen flow was then switched off, and HF was passed over the catalysts at 60 mls/min for one hour at 360° C. The HF was then switched off and the nitrogen purge switched back on to remove any traces of HF.

30 g of 1233zd(Z) was added to a tube with a dip pipe. Nitrogen was passed through the dip pipe and bubbled through the 1233zd(Z). Timed samples were taken of the resulting nitrogen/organic flow and the flow rate could be calculated. 4 mls/min 1233zd(Z) and 15 mls/min nitrogen were passed to the reactors at varying reactor temperatures. Samples of the reactor off gas were analysed by GC and the following results were obtained.

Catalyst 1 (Low Na)

| | Temperature (° C.) | | | | |
|---|---|---|---|---|---|
| | 200 | 225 | 250 | 275 | 300 |
| 1233zd E (mol %) | 43.4 | 58.62 | 75.34 | 79.205 | 83.49 |
| 1233zd Z (mol %) | 56.42 | 40.94 | 24.205 | 19.805 | 13.635 |

Catalyst 2 (High Na)

| | Temperature (° C.) | | | | |
|---|---|---|---|---|---|
| | 200 | 225 | 250 | 275 | 300 | 325 |
| 1233zd E (mol %) | 2.71 | 9.94 | 19.815 | 42.35 | 63.595 | 83.8 |
| 1233zd Z (mol %) | 97.255 | 90.05 | 80.1 | 57.515 | 34.91 | 13.56 |

It is evident from the above that the low sodium catalyst is considerably more active than the corresponding high sodium catalyst for the isomerisation of 1233zd(Z) to 1233zd(E).

EXAMPLE 4

Isomerisation of 1225ye(E) to 1225ye(Z) with Alumina-Supported Chromia Catalysts The same high and low sodium alumina-supported chromia catalysts used in Example 1 were compared in the isomerisation of cis-1,2,3,3,3-pentafluoropropene (1225ye (E)) to trans-1,2,3,3,3-pentafluoropropene (1225ye(Z)).

Both catalysts were dried at 200° C. with 60 mls/min nitrogen for 16 hours, followed by one 25 hour at 360° C. and 60 mls/min $N_2$ to calcine the catalyst The catalysts were then pre-fluorinated, firstly by passing over the catalysts a mixture of HF at 60 mls/min diluted with 60 mls/min nitrogen at 300° C. for one hour. The nitrogen flow was then switched off, and HF was passed over the catalysts at 60 mls/min for one hour at 360° C. The HF was then switched off and the nitrogen purge switched back on to remove any traces of HF. 20 mls/min of 1225ye(E) was then passed over each catalyst at both 230° C. and 260° C., and samples of the reactor off gas were analysed by gas chromatography. The following results were obtained:

| | Temperature (° C.) | |
|---|---|---|
| | 230 | 260 |
| Catalyst 1 (low Na) | | |
| 1225ye Z (mol %) | 50.07 | 72.78 |
| 1225ye E (mol %) | 49.35 | 26.26 |
| Catalyst 2 (high Na) | | |
| 1225ye Z (mol %) | 26.49 | 41.78 |
| 1225ye E (mol %) | 73.48 | 57.81 |

It is evident from the above that the low sodium catalyst is considerably more active than the corresponding high sodium catalyst for the isomerisation of 1225ye(E) to 1225ye(Z).

EXAMPLE 5

Isomerisation of 1234ze(Z) to 1234ze(E) with an Alumina-Supported Zirconia Catalyst A low sodium alumina-supported zirconia catalyst was used for the isomerisation of cis-1,3,3,3-tetrafluoropropene (1234ze(Z)) to trans-1,3,3,3-tetrafluoropropene (1234ze (E)). The catalyst, which is referred to below as catalyst 3, was a low sodium alumina coated/impregnated with zirconia. The catalyst had a sodium content of 353 ppm.

The catalyst was dried at 250° C. with 60 mls/min nitrogen for an hour, followed by one hour at 360° C. with 60 mls/min $N_2$ to calcine the catalyst. The catalyst was then pre-fluorinated, firstly by passing over the catalyst a mixture of HF at 30 mls/min diluted with 60 mls/min nitrogen at 300° C. for one hour. The nitrogen flow was then switched off, and HF was passed over the catalyst at 30 mls/min for one hour at 360° C. The HF was then switched off and the nitrogen purge switched back on to remove any traces of HF.

20 mls/min of 1234ze(Z) (99.97 mol %) was then passed over the catalyst at various temperatures and samples of the reactor off gas were analysed by gas chromatography. The results are shown below.

Catalyst 3

| | Mol % | | Isomer ratio | |
|---|---|---|---|---|
| Temp (° C.) | 1234ze(E) | 1234ze(Z) | 1234ze(E) | 1234ze(Z) |
| 200 | 24.50 | 75.39 | 0.32 | 1.00 |
| 250 | 71.53 | 28.01 | 2.55 | 1.00 |
| 300 | 80.94 | 18.94 | 4.27 | 1.00 |

It is evident from the above that the low sodium alumina-supported zirconia catalyst was effective at isomerising 1234ze(Z) to 1234ze(E).

EXAMPLE 6

Isomerisation of 1234ze(Z) to 1234ze(E) with an Alumina Catalyst

Low sodium alumina was used for the isomerisation of cis-1,3,3,3-tetrafluoropropene (1234ze(Z)) to trans-1,3,3,3-tetrafluoropropene (1234ze(E)). The alumina catalyst (referred to below as catalyst 4) was obtained from BASF and contained 76 ppm.

The catalyst was dried at 250° C. with 60 mls/min nitrogen for an hour, followed by one hour at 360° C. with 60 mls/min nitrogen to calcine the catalyst. The catalyst was then pre-fluorinated, firstly by passing over the catalyst a mixture of HF at 30 mls/min diluted with 60 mls/min nitrogen at 300° C. for one hour. The nitrogen flow was then switched off, and HF was passed over the catalyst at 30 mls/min for one hour at 360° C. The HF was then switched off and the nitrogen purge switched back on to remove any traces of HF.

20 mls/min of 1234ze(Z) (99.97 mol %) was then passed over the catalyst at various temperatures and samples of the reactor off gas were analysed by gas chromatography. The results are shown below.

Catalyst 4

| | Mol % | | Isomer ratio | |
|---|---|---|---|---|
| Temp (° C.) | 1234ze(E) | 1234ze(Z) | 1234ze(E) | 1234ze(Z) |
| 200 | 84.26 | 15.74 | 5.35 | 1.00 |
| 250 | 82.34 | 17.66 | 4.66 | 1.00 |
| 300 | 80.20 | 19.80 | 4.05 | 1.00 |

It is evident from the above that the low sodium alumina catalyst was effective at isomerising 1234ze(Z) to 1234ze (E).

The invention is defined by the following claims.

The invention claimed is:

1. A process for isomerising a $C_{3-7}$ (hydro) (halo)fluoroalkene comprising:
   a) providing a reactor feed stream comprising the $C_{3-7}$ (hydro)(halo)fluoroalkene; and
   b) contacting the $C_{3-7}$ (hydro)(halo)fluoroalkene with a catalyst comprising alumina to isomerise the $C_{3-7}$ hydro (halo)fluoroalkene, wherein the catalyst has a sodium content of less than about 200 ppm, wherein the catalyst comprises a metal oxide supported on the alumina, and wherein the metal is Zr or Cr.

2. The process according to claim 1, wherein the catalyst has a sodium content of less than about 150 ppm.

3. The process according to claim 2, wherein the catalyst has a sodium content of less than about 100 ppm.

4. The process according to claim 3, wherein the catalyst has a sodium content of less than about 80 ppm.

5. The process according to claim 4, wherein the catalyst has a sodium content of less than about 60 ppm.

6. The process according to claim 5, wherein the catalyst has a sodium content of less than about 40 ppm.

7. The process according to claim 6, wherein the catalyst has a sodium content of less than about 30 ppm.

8. The process according to claim 7, wherein the catalyst has a sodium content of less than about 20 ppm.

9. The process according to claim 8, wherein the catalyst has a sodium content of less than about 10 ppm.

10. The process according to claim 1, wherein the catalyst comprises at least 60% by weight of alumina support based on the total weight of the catalyst.

11. The process according to claim 10, wherein the catalyst comprises at least 70% by weight of alumina support based on the total weight of the catalyst.

12. The process according to claim 1, wherein the catalyst comprises up to about 40% by weight of the metal oxide based on the total weight of the catalyst.

13. The process according to claim 12, wherein the catalyst comprises up to about 30% by weight of the metal oxide based on the total weight of the catalyst.

14. The process according to claim 1, wherein the catalyst further comprises at least one additional metal or a compound of the additional metal.

15. The process according to claim 14, wherein the additional metal is selected from the group consisting of Zn, Zr, Cr, In, Co, Ni and mixtures thereof.

16. The process according to claim 14, wherein the catalyst comprises up to about 20% by weight of the at least one additional metal or a compound of the additional metal, based on the total weight of the catalyst.

17. The process according to claim 16, wherein the catalyst comprises up to about 10% by weight of the at least one additional metal or compound of the additional metal.

18. The process according to claim 1, wherein the $C_{3-7}$ (hydro)(halo)fluoroalkene exists as geometric isomers and the isomerising results in a change in a ratio of E and Z isomers of the $C_{3-7}$ (hydro)(halo)fluoroalkene.

19. The process according to claim 1 carried out at a temperature of from 50 to 400° C. and a pressure of up to 30 bara.

20. The process according to claim 19 carried out at a temperature of from 120° C. to 360° C.

21. The process according to claim 1, wherein the $C_{3-7}$ (hydro)(halo)fluoroalkene is isomerised with a conversion of at least about 5%.

22. The process according to claim 1, wherein the $C_{3-7}$ (hydro)(halo)fluoroalkene is a C (hydro) (halo)fluoroalkene.

23. The process according to claim 22, wherein the $CF_{3-6}$ (hydro)(halo)fluoroalkene is a $C_{3-4}$ (hydro)(halo)fluoroalkene.

24. The process according to claim 23, wherein the $C_{3-4}$ (hydro)(halo)fluoroalkene is a (hydro)(halo)fluoropropene.

25. The process according to claim 24, wherein the (hydro)(halo)fluoropropene is a hydrofluoropropene.

26. The process according to claim 25, wherein the hydrofluoropropene is selected from tetrafluoropropenes and pentafluoropropenes.

27. The process according to claim 26, wherein the tetrafluoropropene is 1,3,3,3-tetrafluoropropene (1234ze) and the process comprises isomerising cis-1,3,3,3-tetrafluoropropene (1234ze(Z)) to trans-1,3,3,3-tetrafluoropropene (1234ze(E)).

28. The process according to claim 26, wherein the pentafluoropropene is 1,2,3,3,3-pentafluoropropene (1225ye) and the process comprises isomerising E-1,2,3,3,3-pentafluoropropene (1225ye(E)) to Z-1,2,3,3,3-pentafluoropropene (1225ye(Z)).

29. The process according to claim 24, wherein the (hydro)(halo)fluoropropene is a hydrohalofluoropropene.

30. The process according to claim 29, wherein the hydrohalofluoropropene is 1-chloro-3,3,3-trifluoropropene (1233zd) and the process comprises isomerising cis-1-chloro-3,3,3-trifluoropropene (1233zd(Z)) to trans-1-chloro-3,3,3-trifluoropropene (1233zd(E)).

31. The process according to claim 24, wherein the $C_{3-7}$ (hydro)(halo)fluoroalkene is a hydrohalofluorobutene, a halofluorobutene or a hydrofluorobutene.

32. The process according to claim 31, wherein the hydrofluorobutene is 1,1,1,4,4,4-hexafluorobut-2-ene (1336mzz) and the process comprises isomerising cis-1,1,1,4,4,4-hexafluorobut-2-ene (1336mzz(Z)) to trans-1,1,1,4,4,4-hexafluorobut-2-ene (1336mzz(E)).

33. A process for preparing a $C_{3-7}$ (hydro)(halo)fluoroalkene by dehydrohalogenation of a reactor feed comprising a $C_{3-7}$ hydro(halo)fluoroalkane to produce the $C_{3-7}$ (hydro)(halo)fluoroalkene, and isomerising the $C_{3-7}$ (hydro)(halo) fluoroalkene as defined in claim 1.

34. The process according to claim 33, wherein the reactor feed comprises 1,1,1,3,3-pentafluoropropane (245fa) and the process comprises the following steps:
   (a) dehydrofluorinating 245fa to produce a dehydrohalogenation stream comprising 1234ze(Z), 1234ze(E), HF and, optionally, unreacted 245fa;
   (b) optionally recovering the HF from the dehydrohalogenation stream;
   (c) optionally recovering 1234ze(E) from the dehydrohalogenation stream; and
   (d) contacting the dehydrohalogenation stream with the catalyst comprising a metal oxide supported on alumina to isomerise the 1234ze(Z) to 1234ze(E), wherein the catalyst has a sodium content of less than about 200 ppm.

* * * * *